(12) United States Patent
Huang

(10) Patent No.: US 10,980,971 B2
(45) Date of Patent: Apr. 20, 2021

(54) SURGICAL GUIDE WIRE ASSEMBLY

(71) Applicant: Hsin-Po Huang, Taoyuan (TW)

(72) Inventor: Hsin-Po Huang, Taoyuan (TW)

( * ) Notice: Subject to any disclaimer, the term of this patent is extended or adjusted under 35 U.S.C. 154(b) by 298 days.

(21) Appl. No.: 15/959,418

(22) Filed: Apr. 23, 2018

(65) Prior Publication Data
US 2019/0321586 A1    Oct. 24, 2019

(51) Int. Cl.
*A61M 25/00* (2006.01)
*F16L 3/223* (2006.01)
*A61M 25/09* (2006.01)

(52) U.S. Cl.
CPC .......... *A61M 25/002* (2013.01); *A61M 25/09* (2013.01); *F16L 3/223* (2013.01)

(58) Field of Classification Search
CPC ................ A61M 25/002; A61M 25/09; A61M 25/09041; A61M 25/0113; F16L 3/223
See application file for complete search history.

(56) References Cited

U.S. PATENT DOCUMENTS

| 6,497,670 B1 * | 12/2002 | Parodi ............... A61M 25/0172 600/585 |
| 2004/0055919 A1 * | 3/2004 | Rowe .................. A61M 25/002 206/438 |
| 2016/0074628 A1 * | 3/2016 | Smith .................... A61B 50/20 604/174 |
| 2019/0262577 A1 * | 8/2019 | Anderson .............. A61B 50/30 |

* cited by examiner

*Primary Examiner* — Eric F Winakur
*Assistant Examiner* — Abid A Mustansir
(74) *Attorney, Agent, or Firm* — Bacon & Thomas, PLLC

(57) ABSTRACT

A guide wire assembly includes a dispenser coil, a guide wire and multiple clips. The dispenser coil is resilient and spirally coiled with coiled portions over an entire length of the dispenser coil. The guide wire is resilient and received inside the dispenser coil. The multiple clips are thermally joined to corresponding coiled portions of the dispenser partially over the entire length of the dispenser coil, and are spaced apart from each other by gaps. Each clip is resilient and has multiple circular grooves parallelly formed in and traversing across a bottom of the clip. The dispenser coil is partially thermally joined to the multiple clips and the coiled portions of the dispenser coil are uniformly curved and flush with each other, ensuring that the guide wire assembly can be produced in a time-saving fashion without compromising the capability against deformation to the guide wire.

2 Claims, 9 Drawing Sheets

SURGICAL GUIDE WIRE ASSEMBLY

BACKGROUND OF THE INVENTION

1. Field of the Invention

The present invention relates to a guide wire assembly and, more particularly, to a surgical guide wire assembly with a dispenser tube wound in a coiled form and partially thermally joined to and respectively retained in multiple clips.

2. Description of the Related Art

Surgical guide wires are used in minimally invasive medical applications to position devices such as catheters and stents. As guide wire deformation may suggest complication such as vein or artery perforation, smooth movement of the guide wire inside a human body becomes a critical issue, such that care should be taken to keep guide wires in an undeformed condition to ensure smooth insertability thereof before being used in medical procedures. To address such an issue, how to adequately package guide wires for shipping and storage appears to be one of the most important things to think about since guide wires are long and thin metallic wires.

With reference to FIGS. 5 and 6, a conventional guide wire assembly 30 includes a dispenser coil 31 and a guide wire 32. The dispenser coil 31 is resilient, is made of a thermoplastic material, and is spirally coiled with adjacent coiled portions over the entire length of the dispenser coil 31 joined to each other by thermal bonding. The entire coiled portions are flush with each other when viewed in a sideways viewing direction or in a direction into the cross-sectional view as shown in FIG. 5, and line contact occurs between joined areas of the adjacent coiled portions over the entire dispenser coil 31. The guide wire 32 is resilient and metallic, and is received inside and protected by the dispenser coil 31 against collision and compact. Because the dispenser coil 31 is wound with all the coiled portions thermally bonded in a leveled, seamless and uniformly curved manner, the dispenser coil 31 can prevent torsional and bending stresses as a result of a loosely coiled dispenser coil from acting on the guide wire 32 received in the dispenser coil 31, such that the guide wire 32 is less likely prone to stress-induced deformation. However, the way of thermally bonding adjacent coiled portions over the entire length of the dispenser coil 31 may involve a more complicated and time-consuming production process.

With reference to FIGS. 7 to 9, another conventional guide wire assembly 50 includes a dispenser coil 51, a guide wire 52 and multiple clips 53. The dispenser coil 51 is resilient and is spirally coiled. The guide wire 52 is resilient and metallic, and is received in and protected by the dispenser coil 31. Each clip 53 is resilient, is mounted on coiled portions of the dispenser coil 31, and has multiple sockets 531 longitudinally formed through the clip 53 in a side-by-side fashion. Each socket 531 has a socket mouth 5311 being slit-like and formed through a bottom portion of the socket 531 for the socket 531 to be C-shaped. An arc length across an inner wall of each socket 531 is more than one half of a circumference of the socket 531, such that the coiled portions of the dispenser coil 51 can be pushed into the respective sockets 531 of each clip 53 through the respective socket mouths 5311 for the coiled portion to be held inside the respective sockets 531. The way of packaging the conventional guide wire assembly 50 is less effort-taking simply because what it takes is to use the clips 53 to hold the dispenser coil 51, and there is no additional thermal bonding involved. However, gaps are oftentimes generated between the inner walls of the sockets 531 and corresponding coiled portions of the dispenser coil 51. Besides, the coiled portions are only partially held by the clips 53. All these lead to the coiled portions that are loosely positioned in the sockets 531 of the respective clips 53 and are not flush with each other when viewed in a direction into FIG. 8. The loosely held coiled portions of the dispenser coil 51 may bend and twist the guide wire 52 therein and cause permanent deformation thereto.

SUMMARY OF THE INVENTION

An objective of the present invention is to provide a guide wire assembly capable of being produced in a time-saving fashion without compromising the capability against deformation to the guide wire.

To achieve the foregoing objective, the guide wire assembly includes a dispenser coil, a guide wire and multiple clips.

The dispenser coil is resilient and is spirally coiled with coiled portions over an entire length of the dispenser coil.

The guide wire is resilient and is received inside the dispenser coil.

The multiple clips are resilient, are thermally joined to corresponding coiled portions of the dispenser partially over the entire length of the dispenser coil, and are spaced apart from each other by gaps.

Preferably, each clip has multiple circular grooves parallelly formed in and traversing across a bottom of the clip.

Preferably, the coiled portions of the dispenser coil are partially and thermally joined to inner walls of the multiple circular grooves with line contact occurring between joined portions respectively located on the corresponding coiled portions of the dispenser coil and on the inner walls of the respective circular grooves, and each joined portion takes a form of a segment traversing across a corresponding circular groove of a corresponding clip or across one of the corresponding coiled portions of the dispenser coil.

Preferably, each clip has a flat bottom.

Preferably, the coiled portions of the dispenser coil are partially and thermally joined to flat bottoms of the clips with line contact occurring between joined portions respectively located on the corresponding coiled portions of the dispenser coil and on the flat bottoms of the clips, and each joined portion takes a form of a segment traversing across the flat bottom of a corresponding clip or across one of the corresponding coiled portions of the dispenser coil. Because the dispenser coil is wound with the coiled portions thereof partially thermally joined to the multiple clips and being uniformly curved and flush with each other, the guide wire assembly can get rid of torsional and bending stresses as a result of twisted and bent coiled portion of the dispenser coil. The guide wire received inside the dispenser coil in turn won't easily incur deformation induced from the stresses. Also because the joined portions partially spread over the entire length of the dispenser coil, the guide wire assembly can be produced in a time-saving and efficient fashion without compromising the capability against deformation to the guide wire.

Other objectives, advantages and novel features of the invention will become more apparent from the following detailed description when taken in conjunction with the accompanying drawings.

DETAILED DESCRIPTION OF THE INVENTION

Figure 1:
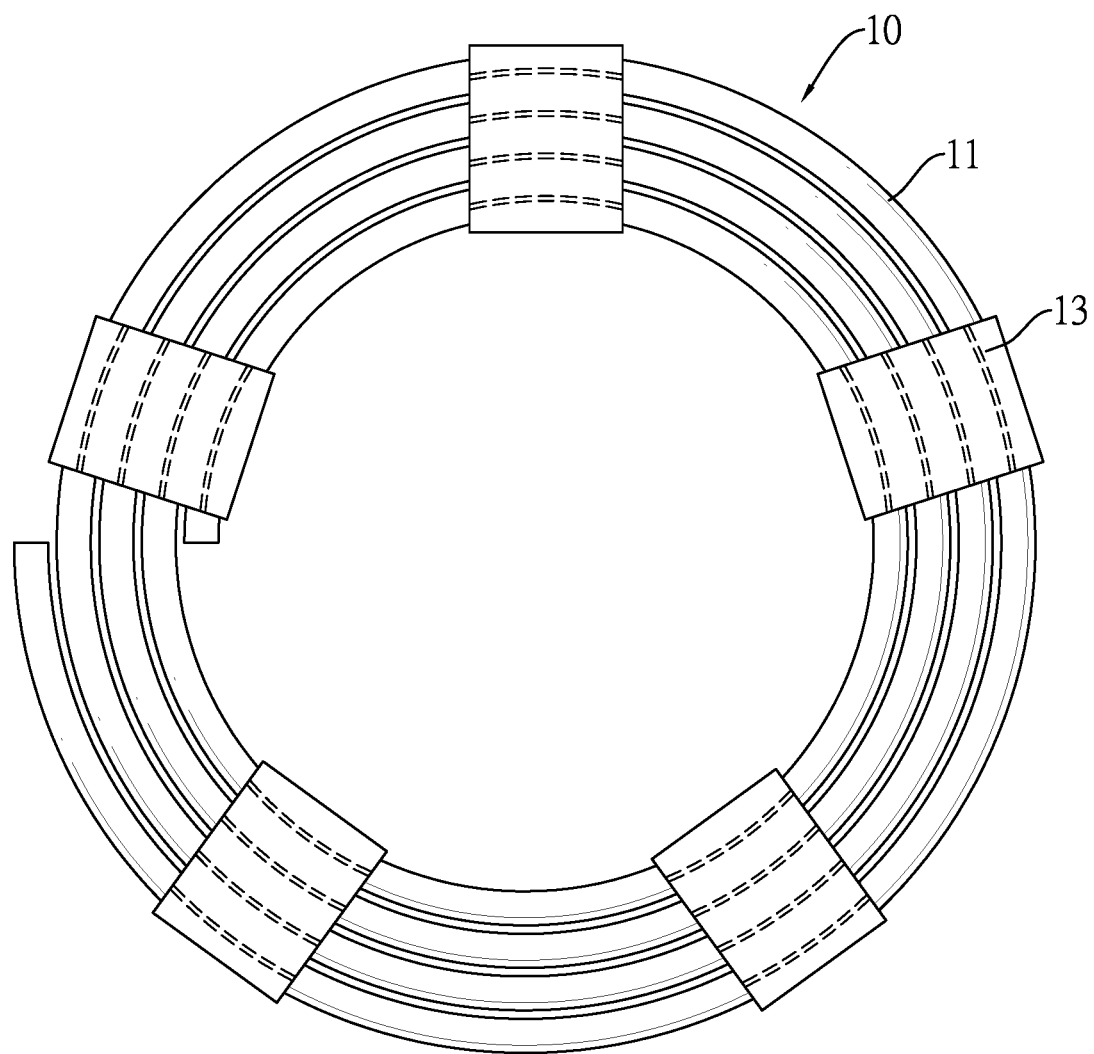
FIG. 1 is a schematic top view of an embodiment of a guide wire assembly in accordance with the present invention.
Figure 2:
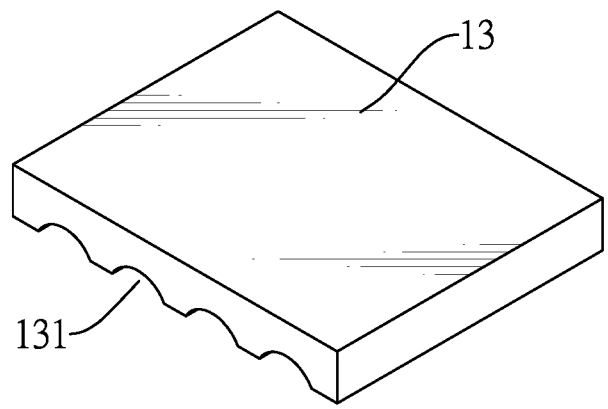
FIG. 2 is a perspective view of a clip of the guide wire assembly in FIG. 1.
Figure 3:
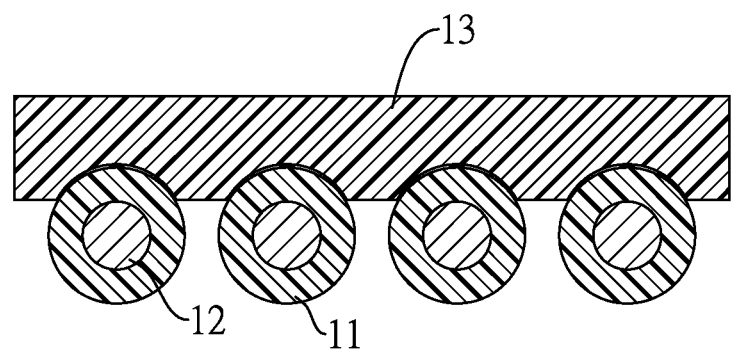
FIG. 3 is a cross-sectional view of the guide wire assembly in FIG. 1.

With reference to FIGS. 1 to 3, an embodiment of a guide wire assembly 10 in accordance with the present invention includes a dispenser coil 11, a guide wire 12 and multiple clips 13. The dispenser coil 11 is resilient, is made of a thermoplastic material, and is spirally coiled with coiled portions over an entire length of the dispenser coil 11. The guide wire 12 is resilient and metallic, and is received inside and protected by the dispenser coil 11. The multiple clips 13 are thermally joined to corresponding coiled portions of the dispenser coil 11 partially over the entire length of the dispenser coil 11, and are spaced apart from each other by gaps. Each clip 13 is resilient, is made of a thermoplastic material, and has multiple circular grooves 131 parallelly formed in and traversing across a bottom of the clip 13.

The entire coiled portions of the dispenser coil 11 are partially and thermally joined to inner walls of the multiple circular grooves 131 with line contact occurring between joined portions respectively located on the corresponding coiled portions of the dispenser coil 11 and on the inner walls of the respective circular grooves 131. Each joined portion takes the form of a segment traversing across a corresponding circular groove 131 of a corresponding clip 13 or across one of the corresponding coiled portions of the dispenser coil 11. Either the circular grooves 131 of the multiple clips 13 or the corresponding coiled portions of the dispenser coil 11 can be selectively heated first and then thermally joined to the other by way of line contact as described earlier. An arc length across the inner wall of each circular groove 131 is less than one half of a circumference of the circular groove 131 to facilitate access to the joined portion of each circular groove 131 and operation on thermally joining the joined portion to the corresponding coiled portions of the dispenser coil 11.

Although the coiled portions of the dispense coil 11 are thermally joined to and held by the respective clips 13 in a partial manner, the joined portions of the dispenser coil 11 and the multiple clips 13 in line contact with each other provide sufficient positioning capability for the coiled portions held by the multiple clips 13 to be flush with each other when viewed in a sideways viewing direction or in a direction into FIG. 3 because the joined portions that are tightly connected with each other introduce no gap formed therebetween. By thermally joining the entire coiled portions of the dispenser coil 11 to the multiple clips 13 by way of line contact over multiple portions of the dispenser coil 11, ends of the coiled portions between each adjacent two of the multiple clips 13 are securely held by the two clips 13, and no gap is formed over the two clips 13 and at the ends of the coiled portion adjacent to the clip 13, such that the coiled portions between the two clips 13 can be uniformly curved and as a result, the entire coiled portions of the dispenser coil 11 can be uniformly curved in a similar way.

Figure 4:
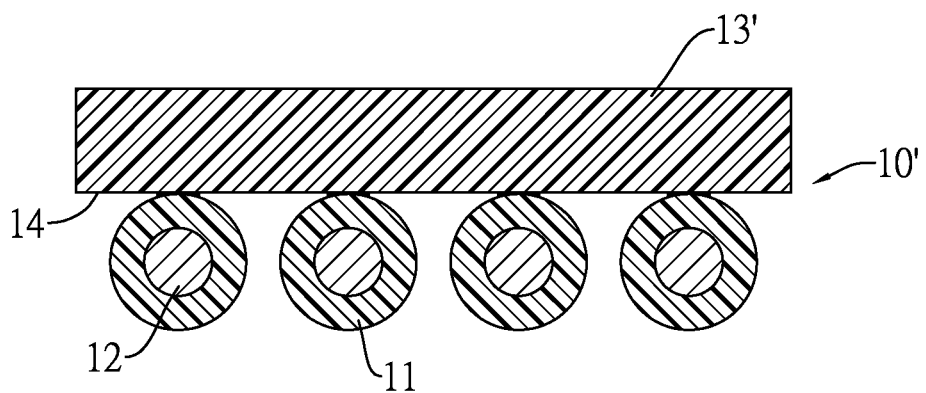
FIG. 4 is a cross-sectional view of another embodiment of the guide wire assembly in accordance with the present invention.
Figure 5:
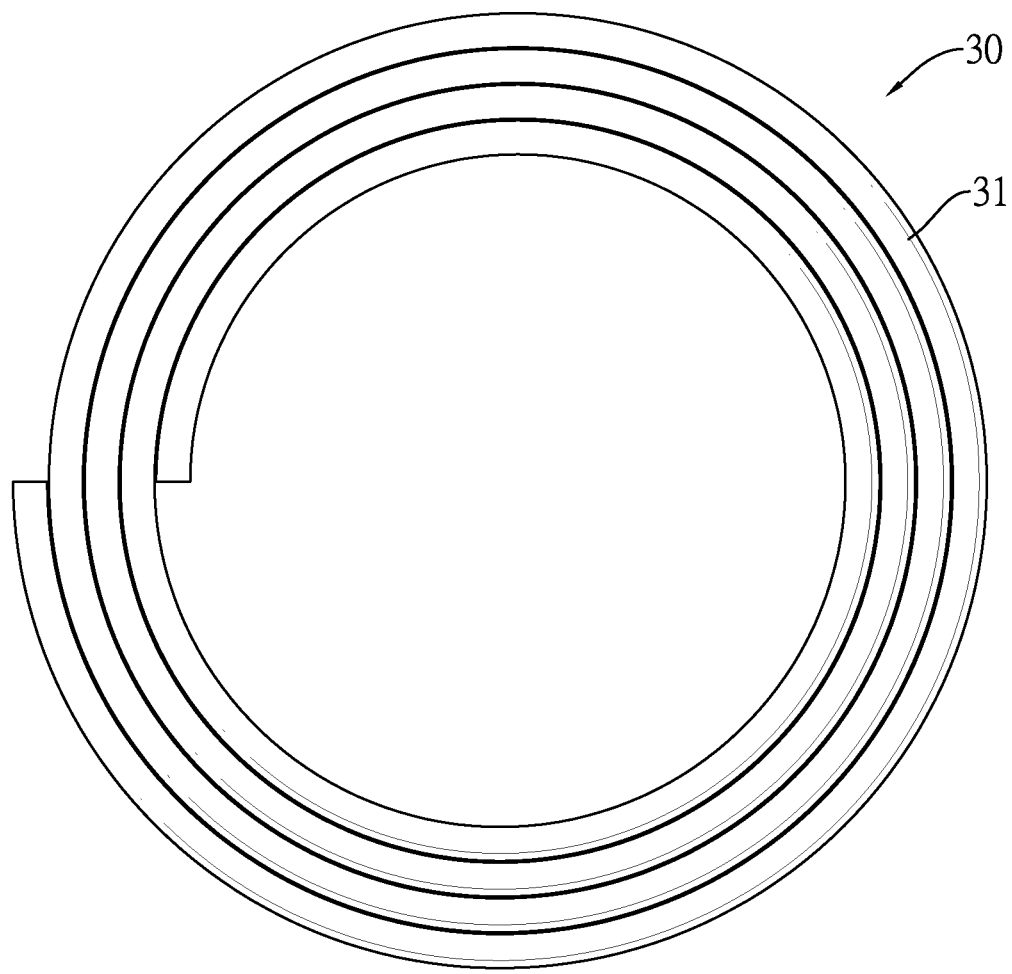
FIG. 5 is a schematic top view of a conventional guide wire assembly.
Figure 6:
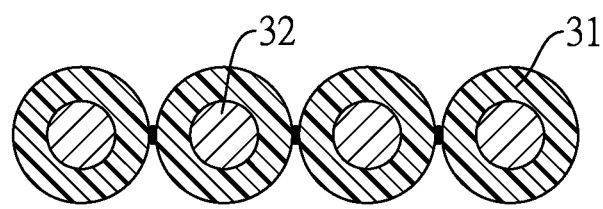
FIG. 6 is a cross-sectional view of the conventional guide wire assembly in FIG. 4.
Figure 7:
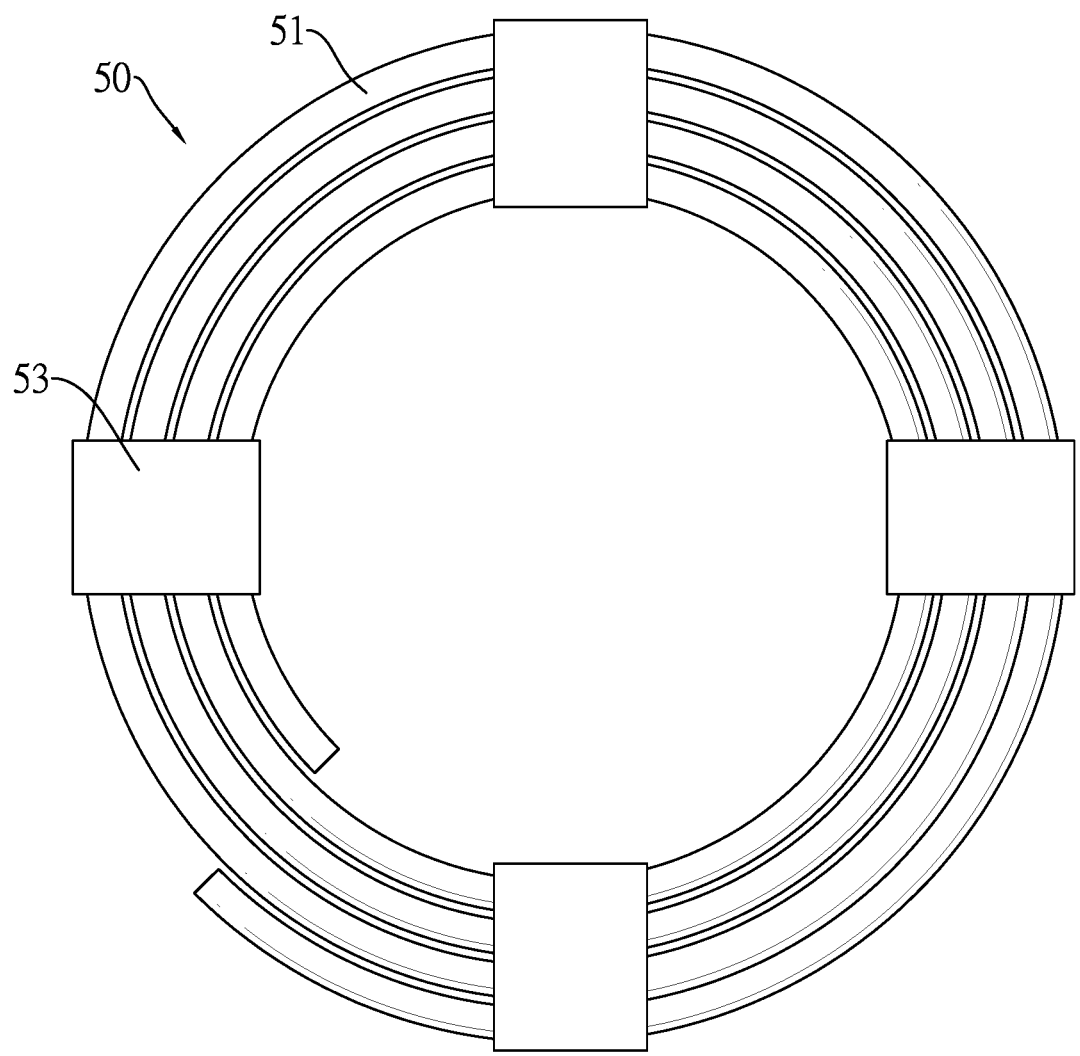
FIG. 7 is a schematic top view of another conventional guide wire assembly.
Figure 8:
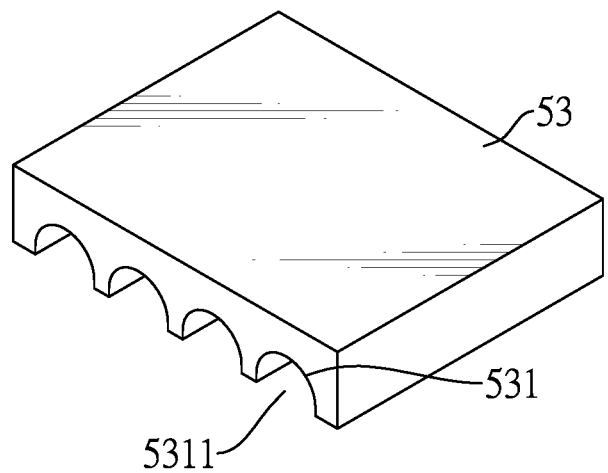
FIG. 8 is a perspective view of a clip of the conventional guide wire assembly in FIG. 7.
Figure 9:
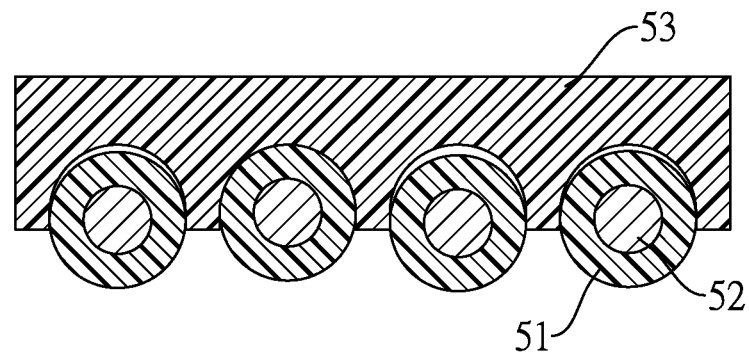
FIG. 9 is a cross-sectional view of the conventional guide wire assembly in FIG. 7.

With reference to FIG. 4, another embodiment of a guide wire assembly 10' in accordance with the present invention is substantially the same as the foregoing embodiment except the shape of multiple clips 13'. The multiple clips 13' are thermally joined to corresponding coiled portions of the dispenser coil 11 partially over the entire length of the dispenser coil 11, and are spaced apart from each other by gaps. Each clip 13' is resilient, is made of a thermoplastic material, and has a flat bottom 14.

The entire coiled portions of the dispenser coil 11 are partially and thermally joined to the flat bottoms 14 of the clips 13' with line contact occurring between joined portions located on the corresponding coiled portions of the dispenser coil 11 and on the flat bottoms 14 of the clips 13'. Each joined portion takes the form of a segment traversing across the flat bottom 14 of a corresponding clip 13' or across one of the corresponding coiled portions of the dispenser coil 11. Either the flat bottom 14 of the multiple clips 13' or the corresponding coiled portions of the dispenser coil 11 can be selectively heated first and then thermally joined to the other by way of line contact.

In sum, the dispenser coil 11, which is wound with the coiled portions thereof partially thermally joined to the multiple clips 13, 13' and being uniformly curved and flush with each other, can prevent torsional and bending stresses generated from twisted and bent coiled portion thereof from acting on the guide wire 12 received in the dispenser coil 11, such that the guide wire 12 is less likely prone to stress-induced deformation. In view of the line contact partially over the joined portions of the dispenser coil 11 being small in area, the guide wire assembly 10 can be produced in a time-saving fashion without compromising the capability against deformation to the guide wire 12.

Even though numerous characteristics and advantages of the present invention have been set forth in the foregoing description, together with details of the structure and function of the invention, the disclosure is illustrative only. Changes may be made in detail, especially in matters of shape, size, and arrangement of parts within the principles of the invention to the full extent indicated by the broad general meaning of the terms in which the appended claims are expressed.

What is claimed is:

1. A guide wire assembly comprising:
    a dispenser coil being resilient and spirally coiled with coiled portions over an entire length of the dispenser coil;
    a guide wire being resilient and received inside the dispenser coil; and
    multiple clips being resilient, thermally joined to corresponding coiled portions of the dispenser coil partially over the entire length of the dispenser coil, and spaced apart from each other by gaps;
    wherein each clip has multiple circular grooves parallelly formed in and traversing across a bottom of the clip;

wherein the coiled portions of the dispenser coil are partially and thermally joined to inner walls of the multiple circular grooves with line contact occurring between joined portions respectively located on the corresponding coiled portions of the dispenser coil and on the inner walls of the respective circular grooves, and each joined portion takes a form of a segment traversing across a corresponding circular groove of a corresponding clip or across one of the corresponding coiled portions of the dispenser coil;

wherein an arc length across the inner wall of each circular groove is less than one half of a circumference of the circular groove.

2. The guide wire assembly as claimed in claim 1, wherein each of the dispenser coil and the multiple clips is made of a thermoplastic material, and the guide wire is metallic.

\* \* \* \* \*